United States Patent [19]

Kesling, Jr.

[11] 4,251,667

[45] Feb. 17, 1981

[54] PROCESS FOR THE PREPARATION OF AROMATIC URETHANES

[75] Inventor: Haven S. Kesling, Jr., Drexel Hill, Pa.

[73] Assignee: Atlantic Richfield Company, Los Angeles, Calif.

[21] Appl. No.: 46,090

[22] Filed: Jun. 6, 1979

Related U.S. Application Data

[63] Continuation-in-part of Ser. No. 882,310, Mar. 1, 1978, abandoned, which is a continuation of Ser. No. 754,069, Dec. 27, 1976, abandoned.

[51] Int. Cl.$^3$ .............. C07C 125/065; C07C 125/073
[52] U.S. Cl. ............................ 560/24; 260/465 D; 560/9; 560/21; 560/22; 560/25; 560/27; 560/28; 560/30; 560/31; 560/32; 560/26; 560/29; 560/33
[58] Field of Search ............. 260/465 D; 560/26, 29, 560/33, 9, 21, 22, 24, 25, 31, 32, 27, 28, 30

[56] References Cited

PUBLICATIONS

T. Saegusa et al., Bull. Chem. Soc., Japan, vol. 42, pp. 2610–2614 (1969).
B. Nefedor et al., Isz. Okad. Nauk. S.S.S.R., Ser Khim, No 9, pp. 1536–1540, 1973.
T. Saegusa et al., Tetrahedron Letters, vol. 49, pp. 6125–6129, 1966.

*Primary Examiner*—Jane S. Myers
*Assistant Examiner*—G. T. Breitenstein
*Attorney, Agent, or Firm*—Coleman R. Reap

[57] ABSTRACT

A process for the preparation of aromatic urethanes by reacting an aromatic amine, an alcohol and carbon monoxide in the presence of a catalytic quantity of a copper salt, oxygen and a dehydrating agent is disclosed. The reaction is preferably carried out using a copper halide catalyst and dehydrating agents which combine with water to release the alcohol used in the preparation of the urethane product.

16 Claims, No Drawings

PROCESS FOR THE PREPARATION OF AROMATIC URETHANES

RELATED APPLICATIONS

This is a continuation-in-part of United States patent application Ser. No. 882,310 filed Mar. 1, 1978, now abandoned, which, in turn, is a continuation application of United States patent application Ser. No. 754,069 filed Dec. 27, 1976, now abandoned.

BACKGROUND OF THE INVENTION

This invention relates to the preparation of urethanes and, more particularly, to the preparation of aromatic urethanes by reaction between aromatic amines, alcohols, and carbon monoxide.

Aromatic urethanes have many important industrial and medical uses, including the preparation of drugs, such as tranquilizers and muscle relaxants, the production of herbicides and insecticides, and the preparation of isocyanates, important building blocks for the production of polyurethanes.

Increasing interest in aromatic urethanes has led to investigations for more economical and efficient processes for their production. Recent research has been directed to the preparation of urethanes by the carbonylation reaction between amines, alcohols, and carbon monoxide using various metal catalysts. Unfortunately, these reactions have been generally catalyzed by expensive Group VIII noble metal catalysts, such as the salts of palladium and platinum. Some success has been observed in the oxidative carbonylation of aliphatic and heterocyclic amines to urethanes with carbon monoxide and alcohols using relatively inexpensive copper salts.

Netherlands Patent No. 94,613 discloses the preparation of urethanes by reacting amines, alcohols and carbon monoxide using copper compound catalysts. Although this patent recommends that the reaction be carried out in the absence of water, there is no teaching of the use of water removal means. Other publications suggest that the presence of water favors carbamate production in this reaction. For example, West German Patent No. 1,105,866 which discloses the preparation of urea compounds by the carbonylation of amines with carbon monoxide using copper compounds, states that drying agents can be added to the reaction mixture to substantially eliminate the production of carbamates.

Since carbon monoxide is a very inexpensive starting material and copper salts are relatively inexpensive catalysts, the preparation of aromatic urethanes from amines, alcohols and carbon monoxide using copper salt catalysts is potentially of considerable economic importance. Accordingly, it would be desirable to adapt this procedure to the preparation of aromatic urethanes from aromatic amines.

SUMMARY OF THE INVENTION

The above-described process has been improved by this invention so that aromatic urethanes can now be prepared by the reaction between aromatic amines, alcohols and carbon monoxide using copper salts as catalysts. Accordingly, it is an object of the invention to present an improved method for the preparation of aromatic urethanes. It is another object of the invention to present a method for preparing aromatic urethanes by the reaction of carbon monoxide, aromatic amines and alcohols. It is another object of the invention to present a method of preparing aromatic urethanes using copper salts as catalysts. It is another object of the invention to present a method for producing aromatic urethanes in high yields by the reaction of aromatic amines, alcohols and carbon monoxide using copper salt catalysts. It is another object of the invention to present a method of preparing aromatic urethanes from aromatic amines, alcohols and carbon monoxide using a regenerating copper catalyst system. These and other objects of the invention will become more obvious from the following description and examples.

The above objects are achieved by reacting aromatic amines, alcohols and carbon monoxide using a copper salt catalyst in the presence of a small amount of oxygen or an oxygen-containing gas mixture and employing means for water removal, such as incorporating dehydrating agents into the reaction mixture. The reaction is generally carried out at a temperature in the range of about 60° to 300° C. and a pressure of about 1 to 700 atmospheres. In preferred embodiments the copper salt is a copper halide, the reaction zone temperature is in the range of about 100° to 250° C., the reaction zone pressure is in the range of about 50 to 150 atmospheres, dehydrating agents which release the alcohol used as a reactant are used, and the amount of oxygen present in the reaction zone is less than the lower limit of the explosive range of mixtures of oxygen and carbon monoxide.

DESCRIPTION OF THE INVENTION

The carbonylation reaction of the invention may be carried out in any high pressure batch-type or continuous reactor. A general procedure is to charge the amine, alcohol, dehydrating agent, catalyst, and the oxygen or oxygen-containing gas mixture into the reaction vessel, introduce the proper amount of carbon monoxide gas to obtain the desired reaction pressure and then heat the mixture to and maintain it at the desired temperature for the appropriate period. The reaction can be carried out batchwise or as a continuous process and the order of addition of the reactants to the reaction vessel may be varied as desired. The reaction products can be conveniently recovered and treated by any conventional method, such as filtration, distillation, etc. to effect separation of the aromatic urethane from unreacted materials, catalyst, by-products, etc.

Any monofunctional or polyfunctional primary, secondary or tertiary aromatic amine or mixture of amines may be used in the process of the invention. The amine reactant has the structural formula

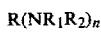

$$R(NR_1R_2)_n$$

wherein R is a carbocyclic aromatic group comprised of 1 to 3 condensed or non-condensed rings, $R_1$ and $R_2$ may be the same or different and either or both may be hydrogen, a saturated or unsaturated aliphatic organic group containing up to 30 carbon atoms or a carbocyclic aromatic group comprised of 1 to 3 condensed or non-condensed rings, and n is at least 1.

R may be unsubstituted or substituted with one or more alkyl groups containing up to 12 carbon atoms each, or other substituents such as halide, hydroxy, ether, ester, mercaptan, thioether, thioester, amino, amido, nitro or nitroso, etc., substituents or organic groups containing these substituents.

When $R_1$ and $R_2$ are aliphatic organic groups, they can be hydrocarbons or can contain one or more of the substituents enumerated above as being optionally present in R. When they are not aromatic they are preferably hydrogen or alkyl groups having up to 12 carbon atoms. When $R_1$ or $R_2$ are aromatic groups they can be any of the groups mentioned in defining R and may be the same as or different from R.

When n is 1 the amine is monofunctional and when n is greater than 1 the amine is polyfunctional. Preferred amines are those in which n is 1 to 3.

If it is desired, a mixture of two or more aromatic amines may be used as the amine reactant. Also, the reaction mixture can contain one or more aliphatic or heterocyclic amines in addition to the aromatic amine reactant.

Representative aromatic amines include aniline, diphenyl amine, triphenyl amine, N-methylaniline, N,N-dimethylaniline, N-methyl-N-ethylaniline, the toluidines, N-methyl-o-toluidine, N,N-dimethyl-p-toluidine, etc., the xylidines, N-methyl-N-ethyl-xylidine, N-methyl-p-hexylaniline, N-heptyl-m-pentylaniline, chloroaniline, N-methyl-p-bromoaniline, nitroaniline, nitrosoaniline, cyanoaniline, methoxyaniline, N-pentyl-o-nitroaniline, p-hydroxyethylaniline, N,N-dimethyl-m-mercaptopropylaniline, the phenylene diamines, the toluene diamines, N, N-diphenylamine, N-propyl-N-toluidinylaniline, 4,4'-diaminodiphenylmethane, α-naphthylamine, β-naphthylamine, 1,5-diaminonaphthene, etc. The preferred aromatic amines are the mononuclear aromatic amines, such as aniline, N-methylaniline, N,N-dimethylaniline, phenylamine diamine, etc.

The alcohol component used in the process of the invention has the structural formula

$R(OH)_n$ wherein R is a mono- or polyfunctional aliphatic aromatic or cycloaliphatic organic group usually having 1 to 20 carbon atoms, and n is at least 1. When R is aliphatic or cycloaliphatic it preferably has 1 to 12 and most preferably 1 to 8 carbon atoms. When R is aromatic it is usually comprised of 1 to 3 condensed or non-condensed rings and is preferably comprised of one aromatic ring. R can be unsubstituted, i.e., a hydrocarbon group, or it can contain atoms other than hydrogen or carbon in its main chain or in groups pendent from the main chain. These substituents do not substantially interfere with the reaction of the invention. Typical substitutents present in alcohols useful in the invention include halogen atoms and ether, ester, amino, amido, cyano, nitro, nitroso, mercapto, thioester carboxy, alkoxy, etc., groups. When n is 1 the alcohol is monofunctional and when n is greater than 1 the alcohol is polyfunctional. In preferred embodiments n varies from 1 to 6 and most preferably from 1 to 3.

Representative alcohols within the scope of the above description include methanol, ethanol, n-, iso-, sec-and tert-butanol, amyl alcohol, hexanol, lauryl alcohol, cetyl alcohol, allyl alcohol, oleyl alcohol, 3-chloroheptanol, ethoxyethanol, cyclohexanol, methylcyclohexanol, cyclohexanol, phenol, benzyl alcohol, chlorobenzyl alcohol, cresol, o-nitrobenzyl alcohol, p-aminophenol, anisyl alcohol, β-naphthol, 1,4-butanediol, ethylene glycol, 1,3-propanediol, 1,4-cyclohexanediol, etc. The preferred alcohols are the mono and difunctional saturated aliphatic or cycloaliphatic alcohols containing up to 8 carbon atoms, such as methanol, ethanol, butanol, cyclohexanol, and ethylene glycol and aromatic alcohols comprised of one aromatic ring, such as benzyl alcohol, phenol, and 2,4-toluenediol.

The equivalents ratio of total aromatic amine to alcohol is not critical, but is usually about 0.8:1 to 2.2:1 and preferably about 0.9:1 to 1.1:1.

The copper salts usable as catalysts in the process of the invention include copper(I) and copper(II) salts and mixtures of these. In general, any copper salt usable as a catalyst can be used in the invention. The copper salt anions may be inorganic, such as the halides, sulfates, sulfites, nitrates, nitrites, carbonates, etc.; or organic, such as acyl groups, including acetate, formate, propionate, alkoxides such as methoxide, ethoxide, etc.

Examples of representative copper salts are copper(I) chloride, copper(II) chloride, copper(I) bromide, copper(II) bromide, copper(II) iodide, copper(II) formate, copper(II) acetate, copper(I) propionate, copper(II) methoxide, copper(I) ethoxide, etc. The preferred copper salts are the halides, particularly the copper(II) halides, such as copper(II) chloride and copper(II) bromide.

The amount of catalyst used in the reaction may vary from the minimum amount which is catalytically effective up to about 15%, based on the total weight of aromatic amine present in the reaction zone. Amounts greater than about 15% can be used, if desired, however, the efficiency of the reaction decreases as larger amounts of catalyst are employed. The amount of copper salt catalyst usually used in the process of the invention varies from about 0.01 to about 15%, and preferably from about 0.1 to about 5%, based on the total weight of aromatic amine present in the reaction zone.

A ligand or coordination complex compound of the metal catalyst can be included, if desired, in the catalyst formulation to modify the properties of the copper salt catalyst. Examples of suitable compounds include organic ligands, such as alkyl or aryl phosphines or phosphine oxides, arsines or stibines, heterocyclic amines such as pyridine, and inorganic ligands, such as tin chloride, etc. When these agents are included they are often used in amounts up to about four molar equivalents of ligand per mole of copper.

The reaction is carried out in the presence of a catalyst oxidizing agent. During the reaction between the carbon monoxide and the aromatic amine, the copper(II) ions are reduced to copper(I) ions. The oxidizing agent functions to oxidize the copper(I) back to the copper(II) state. It is not known what additional part the oxidizing agent plays in he process of the invention, but it has been discovered that aromatic amines will not react with carbon monoxide to produce aromatic formamides in the absence of an oxidizing agent, such as oxygen. Suitable oxidizing agents include oxygen or other suitable oxidizing agents, such as quinone. When oxygen is used it may be introduced as pure oxygen or as a component in a gas mixture, such as air. The amount of oxygen present in the reaction zone at any given time is preferably such that the concentration of oxygen is less than 6.1 volume percent. This is the lower limit of the explosive range of oxygen in carbon monoxide as determined from the tables on pages 1771–1772 of the Handbook of Chemistry and Physics, 37th Edition, 1955. Although the reaction can be carried out at oxygen levels of 6.1 volume percent or greater, it is preferred to keep the oxygen and carbon monoxide levels at safe concentrations to avoid the hazard of an explosion.

During the course of the reaction between the aromatic amine, alcohol and carbon monoxide, the reoxidation of copper(I) to copper(II) produces water as a by-product. Although water can usually be tolerated when aliphatic urethanes are prepared by the reaction used in this invention, it has been discovered that aromatic amines will not react with alcohols and carbon monoxide to produce aromatic urethanes unless the reaction is carried out under conditions such that the water formed during the reaction process is removed from the reaction zone. In the present invention this is accomplished by process techniques, such as azeotropic distillation or by carrying out the reaction in the presence of dehydrating agents. When azeotropic distillation is employed the water can be removed with a portion of the alcohol or other solvent. Suitable azeotropic mixtures are those formed between alcohols and water. It is preferable to use dehydrating agents in the process of the invention. Especially preferred dehydrating agents are those which react chemically with water to release alcohols as exemplified by the following reactions:

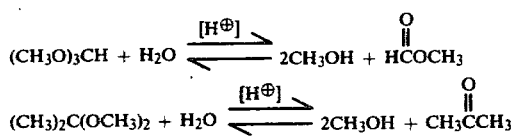

Suitable dehydrating agents include orthoesters, ketals, acetals, enolethers, trialkylorthoborates. Preferred dehydrating agents are those which will release lower alcohols, i.e., aliphatic or cycloaliphatic alcohols having up to 8 carbon atoms in their structures, upon reaction with water. Particularly suitable dehydrating agents are those which, upon contact with water, release the particular alcohol from which the urethanes is being prepared. Examples of preferred dehydrating agents are trimethylorthoformate, triethylorthoformate, tributylorthoformate, 2,2-dimethoxypropane, 2,2-di-n-butoxypropane, 1,1-dimethoxycyclohexane, 1,1-di-n-butoxycyclohexane, 1,1-dimethoxymethane, 1,1-diethoxyethane, 1-methoxyethane, 2-ethoxyprop-2-ene, 1-methoxycyclohex-1-ene, trimethylborate. The most preferred dehydrating agents are the orthoesters and ketals which react with water to release alcohols having up to 6 carbon atoms in their structures. It is most preferred that the alcohol being released be the alcohol which is used as the reactant.

The reaction can be carried out with or without a solvent. However, it is preferred to use a solvent. When lower molecular weight amines and excess alcohol are reacted there is no need for additional solvents. However, in some cases, for example when higher molecular weight reactants are used, it may be desirable to conduct the reaction in the presence of a solvent. Preferred solvents are the non-oxidizable polar solvents, such as methyl acetate, chlorobenzene, etc. It is usually preferred to use a sufficient quantity of solvent to completely dissolve the reactants and to prevent localized overheating. The optimum amounts for each reaction system can be easily determined.

The following examples illustrate specific embodiments of the invention. Unless otherwise indicated parts and percentages are on a weight basis.

EXAMPLE I

A solution of 23.28 g (250 mmole), aniline, 53.06 g (500 mmole) trimethylorthoformate, and 60.00 g of absolute methanol was charged into the autoclave along with 3.36 g (25 mmole) anhydrous copper(II) chloride. The autoclave is sealed and charged with carbon monoxide to a pressure of 1600 psig. The temperature in the autoclave is raised to and maintained at 125° C. The reaction is initiated by charging oxygen into the autoclave until the pressure reaches 1700 psig. The gas charge line is then flushed by charging carbon monoxide into the reactor until the autoclave pressure reaches 1800 psig. A considerable pressure drop is observed over the course of the 2 hour reaction period. GLC (gas-liquid chromatography) and ALC (analytical liquid chromatograph) analyses indicate that 29.54 g (195.6 mmole) of methyl-N-phenylcarbamate is formed. Based on aniline as a limiting reactant, a selectivity of 81.6 mole % to methyl-N-phenylcarbamate at 95.9% aniline conversion is obtained.

EXAMPLE II

The procedure of Example I is repeated except that no trimethylorthoformate is employed. No pressure drop is observed over the course of a four hour residence period. GLC and ALC analyses indicate that no methyl-N-phenylcarbamate is formed. Most of the aniline initially charged is recovered unchanged.

EXAMPLE III

The procedure of Example I is repeated except that 26.75 g (250 mmole) N-methylaniline is substituted for the aniline. A pressure drop of 1580 psi over the course of a two hour period is observed. GLC and ALC analyses indicate the presence of 27.62 g (167.4 mmole) of methyl-N-methyl-N-phenylcarbamate. Based on N-methylaniline as a limiting reagent, a selectivity of 72 mole % to methyl-N-methyl-N-phenylcarbamate at 93% N-methylaniline conversion is obtained.

EXAMPLE IV

The procedure of Example I is repeated except that 24.75 g (125 mmole) of 4,4'-diaminodiphenylmethane is substituted for the aniline and 1.68 g (12.5 mmole) anhydrous copper(II) chloride is used. a strong exotherm and a rapid pressure drop of about 1475 psi over the course of a two hour resistance period is observed. GLC and ALC analyses indicate that 31.03 g (98.8 mmole) of diphenylmethane-4,4'-bis(methylurethane)(MDIU) is formed. Based on 4,4'-diaminodiphenylmethane as a limiting reagent, a selectivity of 85 mole % to MDIU at 93% diaminodiphenylmethane conversion is obtained.

EXAMPLE V

The procedure of Example I is repeated except that benzyl alcohol is substituted for the methanol and tribenzylorothoformate is substituted for the trimethylorthoformate. GLC and ALC analyses will indicate the formation of substantial amounts of benzyl-N-phenylcarbamate.

EXAMPLE VI

The procedure of Example I is repeated except that 15.25 g (125 mmole) of 2,4-diaminotoluene is substituted for the aniline and a mixture of 4.12 g (25 mmole) anhydrous copper(II) sulfate and 1.68 g (12.5 mmole) of copper(II) chloride is used as the catalyst. A pressure drop of 1275 psi over the course of a two hour period is observed. GLC and ALC analyses indicate the pressure of 18.41 g (77.3 mmole) of toluene-2,4-bis(methylcarbamate) (TDIU). Based on 2,4-diaminotoluene as a limiting reagent, a selectivity of 68 mole % of TDIU at 91% 2,4-diaminotoluene conversion is obtained.

EXAMPLE VII

The procedure of Example I is repeated except that 35.79 g (250 mmole) 2-naphthylamine is substituted for the aniline and 4.12 g (25 mmole) anhydrous copper(II) sulfate and 0.55 g (2.8 mmole) anhydrous copper(I) iodide is substituted for the copper(I) chloride. GLC and ALC analyses will indicate the presence of substantial amounts of methyl-N-(2-naphthyl)urethane.

EXAMPLE VIII

The procedure of Example I is repeated except that p-chloroaniline is substituted for the aniline, cyclohexanol is substituted for the methanol and 2,2-tricyclohexylpropane is substituted for trimethylorthoformate, GLC and ALC analyses will indicte the presence of substantial amounts of cyclohexyl-N-p-chlorophenylurethane.

Although the invention has been described with particular reference to specific examples, it is understood that the scope of the invention is not limited thereto but is only determined by the breadth of the appended claims.

I claim:

1. A process for the preparation of aromatic urethanes which comprises reacting at a temperature of about 60° to 300° C. and a pressure of about 1 to 700 atmospheres, an aromatic amine, an alcohol and carbon monoxide in the presence of a salt selected from copper I and copper II salts and mixtures of these, oxygen or an oxygen-containing gas present in an amount less than the minimum amount necessary to form an explosive mixture of carbon monoxide and oxygen and a dehydrating agent.

2. The process of claim 1 wherein the copper salt is present in an amount of about 0.01 to 15% based on the total weight of aromatic amine present.

3. The process of claim 2 wherein the copper salt is an inorganic salt.

4. The process of claim 3 wherein the copper salt is a copper halide.

5. The process of claim 4 wherein the copper halide is present in an amount of about 0.1 to 5% based on the total weight of aromatic amine present.

6. The process of claim 4 wherein the copper halide is copper chloride.

7. The process of claim 1 wherein the dehydrating agent releases an alcohol upon reaction with water.

8. The process of claim 7 wherein the alcohol released by the dehydrating agent is the same as the alcohol used as reagent.

9. The process of claim 7 wherein the dehydrating agent is a member of the group consisting of orthoesters, ketals, acetals, enolethers, trialkylorthoborates, and mixtures of these.

10. The process of claim 1 wherein a non-oxidizable organic polar solvent is present in the reaction zone.

11. A process for the preparation of aromatic urethanes which comprises reacting at a temperature of about 60° to 300° C. and a pressure of about 1 to 700 atmospheres, an aromatic amine, an alcohol and carbon monoxide in the presence of about 0.01 to 15%, based on the total weight of aromatic amine present, of a copper halide catalyst selected from copper I halide, copper II halide and mixtures of these, oxygen in amount less than the minimum amount necessary to form an explosive mixture of carbon monoxide and oxygen, and an organic dehydrating agent selected from the group consisting of orthoesters, ketals, acetals, enolethers and orthoborates which, when hydrolyzed with water, release the same alcohol that is used as a reactant.

12. The process of claim 11 wherein the copper halide catalyst is copper chloride or copper bromide or mixtures of these and it is present in an amount of about 0.1 to 5%, based on the total weight of aromatic amine present.

13. The process of claim 12 wherein the alcohol is selected from aliphatic alcohols having 1 to 8 carbon atoms, cycloaliphatic alcohols having up to 8 carbon atoms and aromatic alcohols comprised of 1 aromatic ring.

14. The process of claim 13 wherein said aromatic amine is aniline, a substituted aniline, or a phenylene diamine.

15. The process of claim 13 wherein said dehydrating agent is an orthoester or a ketal.

16. The process of claim 14 wherein the alcohol is methanol, ethanol, propanol, or butanol.

* * * * *